United States Patent [19]

Nojiri et al.

[11] Patent Number: 4,812,437

[45] Date of Patent: Mar. 14, 1989

[54] SILVER-DEPOSITED CATALYST FOR PRODUCTION OF ETHYLENE OXIDE

[75] Inventors: Naohiro Nojiri, Tsuchiura; Yukio Sakai; Tomoatsu Iwakura, both of Ami, all of Japan

[73] Assignee: Mitsubishi Petrochemical Co., Ltd., Tokyo, Japan

[21] Appl. No.: 46,177

[22] Filed: May 5, 1987

[30] Foreign Application Priority Data

May 9, 1986 [JP] Japan .................................. 61-104950

[51] Int. Cl.$^4$ ........................ B01J 21/12; B01J 23/02; B01J 23/04; B01J 23/50
[52] U.S. Cl. .................................... 502/243; 502/341; 502/348
[58] Field of Search ................ 502/243, 341, 347, 348

[56] References Cited

U.S. PATENT DOCUMENTS

| | | | |
|---|---|---|---|
| 4,207,210 | 6/1980 | Kilty | 502/348 |
| 4,419,276 | 12/1983 | Bhasin et al. | 502/347 |
| 4,471,071 | 9/1984 | Rebsdat et al. | 502/348 X |

Primary Examiner—W. J. Shine
Attorney, Agent, or Firm—Wenderoth, Lind & Ponack

[57] ABSTRACT

A silver-deposited catalyst for production of ethylene oxide by oxidizing ethylene, having high selectivity and long life, is provided by this invention. The catalyst is characterized by a combination of (a) catalyst ingredients comprising silver and a cation component selected at least from sodium, potassium, rubidium and cesium, and (b) a carrier composed mainly of alpha-alumina, said carrier having a surface area of 0.6 to 2 m$^2$/g, a water absorption of 20 to 50%, a silica content of 0.5 to 12% by weight, a silica content, per m$^2$/g of surface area, of 0.5 to 12, preferably 1 to 8, and a sodium content of 0.08 to 2% by weight.

12 Claims, No Drawings

SILVER-DEPOSITED CATALYST FOR PRODUCTION OF ETHYLENE OXIDE

This invention relates to a silver-deposited catalyst for producing ethylene oxide by vapor-phase oxidation of ethylene.

Annual world production of ethylene oxide amounts to as much as several million tons. In order to produce ethylene oxide efficiently, it has been strongly desired to develop improved catalysts having high selectivity and long active lives, and various methods have been proposed. Most of these methods are directed to optimization of the combination of silver as a main active ingredient with an additive such as an alkali and the proportions of these ingredients, and to improvement of carriers for supporting these ingredients. One aim of the latter-mentioned type of method would be to obtain high selectivity and long life by increasing the specific surface area of the carrier and thereby improving the dispersion of silver and enabling the resulting catalyst to be used at low temperatures. The desired effect, however, cannot be obtained by simply increasing the surface area of the carrier because small particles used to increase the surface area of the carrier form narrow pores inside the carrier and this inhibits diffusion of the reaction gas mixture in the pores. Hence, such methods require further improvement.

For example, in the technique disclosed in Japanese Laid-Open Patent Publication No. 89843/1981, an alpha-alumina carrier having a sodium content of as low as 0.07% by eight or less is selected and used as a carrier having a surface area of 0.5 to 5 $m^2/g$, and by combining this carrier with 5 to 25% by weight of silver and 0.001 to 0.05 gram-equivalent of at least one alkali metal selected from potassium, rubidium and cesium, a good catalyst is obtained.

The present inventors have made extensive investigations on a carrier having a high surface area in order to produce a catalyst having high selectivity and a long life. These investigations have led t the discovery that to obtain a catalyst having high activity and high selectivity for the production of ethylene oxide, the combination of catalyst ingredients and a carrier is important, and a catalyst of such high performance can be obtained by combining a carrier having a silica content of a specific range which has not attracted attention previously, particularly a silica and a sodium content within specific ranges, with silver and a specific cation component as catalyst ingredients. It has particularly been found in accordance with this invention that the action of sodium added as the cation component is characteristic, and by combining it with at least one of potassium, rubidium and cesium, and preferably barium as well, a catalyst capable of exhibiting high performance can be obtained.

The present invention provides (1) a silver-deposited catalyst for production of ethylene oxide by oxidizing ethylene comprising as catalyst ingredients silver and a cation component selected at least from sodium, potassium, rubidium and cesium, and a carrier composed mainly of alpha-alumina, said carrier having a surface area of 0.6 to 2 $m^2/g$, a water absorption of 20 to 50%, a silica content of 0.5 to 12% by weight, a silica content, per $m^2/g$ of surface area, of 0.5 to 12, preferably 1 to 8% by weight, and a sodium content of 0.08 to 2% by weight;

(2) a catalyst according to (1) wherein the cation component is composed of (A) sodium and (B) at least one of potassium, rubidium and cesium;

(3) a catalyst according to (1) wherein the cation component is composed of (A) sodium, (B) at least one of potassium, rubidium and cesium and (C) barium;

(4) a catalyst according to (1) wherein the cation component has been deposited on the carrier from aqueous solution; and (5) a catalyst according to (1) wherein during production of said catalyst, silver and/or the cation component is impregnated in the carrier and heat-treated in superheated steam at 130° to 300° C.

The reason for the high performance of the catalyst of this invention is not entirely clear. It has been found that (1) X-ray diffraction shows that in the carrier used in tnis invention, $Al_6Si_2O_{13}$ is formed besides alpha-$Al_2O_3$;

(2) the carrier used in this invention has acidity that can be detected by an indicator having a pKa of +4.8 (the acidity is measured in accordance with page 161 et seq. of Tanabe and Takeshita, "Acid Base Catalysts", published on Apr. 26, 1966 by Sangyo Tosho K. K.); and (3) the acidity of the carrier disappears when $Na_2CO_3$ is deposited on it and basicity appears under which the color of Bromothymol Blue having a pKb of +7.1 is changed.

On the basis of these facts, it is presumed that the carrier used in the catalyst of this invention exhibits acidity which can be detected by an indicator having a pKa of +4.8 as a result of containing silica, particularly silica and sodium in amounts within specified ranges, that the acidity is moderately controlled by the addition of the cation component as a catalyst ingredient, and that by the synergistic effect of these, the catalyst exhibits its very high performance.

The silver compound used to form silver as a catalytic ingredient in this invention may be any silver compound which forms with an amine a complex soluble in an aqueous solvent and decomposes at a temperature of not more than 500° C., preferably not more than 300° C., more preferably not more than 260° C., to deposit silver. Examples are silver oxide, silver nitrate, silver carbonate and silver carboxylates such as silver acetate and silver oxalate. The amine as a complex-forming agent may be any amine which can solubilize the silver compound in an aqueous solvent. Examples are pyridine, acetonitrile, ammonia and amines having 1 to 6 carbon atoms. Ammonia, pyridine, monoamines such as butylamine, alkanolamines such as ethanolamines, alkylenediamines having 2 to 4 carbon atoms, and polyamines are preferred. Ethylenediamine and 1,3-propanediamine, particularly a mixture of both, are especially preferred.

For impregnation in the carrier, it is most practical to use the silver compound in the form of an aqueous amine solution. An aqueous solution containing an alcohol, for example, may also be used. The concentration of silver in the impregnating solution is selected so that 5 to 25% by weight of silver is deposited finally as a catalytic ingredient. The impregnating operation is carried out by an ordinary method. If required, pressure reduction, heating, spraying, etc. are also carried out. The amine is added in an amount required to complex the silver compound (usually, two amino groups correspond to one silver atom). Usually, it is safe to add it in an amount exceeding the equivalent weight by 5 to 30%.

Heat-treatment after the impregnation is carried out by selecting such a temperature and time as are required to deposit silver on the carrier. It is most desirable to select such conditions as to allow silver to exist on the carrier as fine particles as uniformly as possible. Generally, high temperatures and long periods of time are undesirable because they promote aggregation of the deposited silver particles. Preferably, calcination is carried out for as short as 5 to 30 minutes by using air (or an inert gas such as nitrogen) heated at 120° to 300° C. or superheated steam. The calcination for a short period of time is also desirable since it shortens the time required for catalyst preparation. In particular, the use of superheated steam is desirable as it makes the distribution of silver on the carrier uniform.

The cation component as a catalytic ingredient is preferably added in the form of a compound soluble in an aqueous solvent in a soluble concentration. It may, however, remain partly insoluble. Examples of such compounds are inorganic salts such as nitrates, carbonates, bicarbonates, halides, hydroxides, nitrites and sulfates, and carboxylates such as formates. The halides as the cation component are preferably added so that 5 ppm to 0.1% by weight, preferably 7 ppm to 0.07% by weight, of a halogen such as chlorine, bromine or fluorine, particulary chlorine, is contained as a catalytic ingredient in the final catalyst. The cation component may be added to the silver impregnating solution and deposited (simultaneous impregnation). Or it may be impregnated before or after deposition of the silver. After-impregnation, however, is unsuitable in the case of sodium. An aqueous solution is preferred as the impregnating solution. The use of a solution containing an alcohol, for example, is not recommendable from the standpoint of safety and simplification of process steps.

Sodium as a catalytic ingredient is preferably contained in an amount of 50 ppm to 1% by weight in the catalyst. Its optimum amount varies depending upon the silica content. Advantageously, it is generally 500 to 4,000 ppm. It is especially preferred to apply it in the form of sodium carbonate or sodium bicarbonate.

The content of the alkali metal component selected from potassium, rubidium and cesium is preferably 10 to 2,000 ppm, particularly 75 to 300 ppm for potassium, 160 to 650 ppm for rubidium and 250 to 1,000 ppm for cesium. Most preferably, the alkali metal component is impregnated simultaneously with the impregnation of the silver compound. Preferably, it is added partly or wholly as a halide such as a chloride, bromide or fluoride, particularly the chloride. Preferably, barium is added in an amount of 30 to 1,000 ppm, preferably 40 to 650 ppm, to the catalyst. Suitably, it is added in the form of a nitrate or hydroxide, for example.

When the cation component as a catalytic ingredient is added by a method other than the simultaneous impregnation, it is preferably deposited on the carrier by drying it for 5 to 30 minutes with superheated steam at 110° to 200° C. This operation enables the cation component to be uniformly dispersed in the carrier.

The carrier is preferably molded into the shape of a sphere, a pellet, a ring, etc. having a size of about 3 to 10 mm. Preferably, it is composed mainly of alphaalumina. The carrier further has a surface area of 0.6 to 2 $m^2/g$, preferably 0.8 to 1.7 $m^2/g$. The carrier advantageously has a water absorption of 20 to 50%, preferably 25 to 45%, in order to retain strength and this specific surface area and facilitate the impregnating operation. Pores having a size of less than 0.1 micrometer are undesirable for production of ethylene oxide. Good results cannot be obtained with average pore diameters of less than 0.9 micrometer, particularly less than 0.5 micrometer. Too large an average pore diameter cannot give the required surface area. Hence, the average pore diameter of the carrier used in the invention is preferably 0.9 to 3.5 micrometers, more preferably 1 to 3 micrometers.

The carrier contains 0.5 to 12% by weight, preferably 1 to 12% by weight, more preferably 2 to 10% by weight, of silica. The inclusion of silica increases the strength of the carrier.

The silica content per $m^2/g$ of the surface area is considered to be one measure of the acid amount on the surface of the carrier. If it is too small, the acid amount on the surface is small, and the intended effect does not appear. On the other hand, if it is too large, it does not lead to an increase in the acid amount, but rather causes deleterious side effects such as the decrease of the surface area and streng th of the carrier and the nonuniformity of the pores. Hence, it is advantageously 0.5 to 12, preferably 1 to 8, % by weight/$m^2/g$.

There is no particular limitation on the content of sodium included initially in the carrier. It has been found however in accordance with this invention that a carrier containing 0.08 to 2% by weight of sodium (as Na) in addition to silica and showing acidity that can be detected by an indicator having a pKa of +4.8 is very effective for making a catalyst having high activity and high selectivity. Preferably, the sodium content of the carrier is 0.1 to 1.5% by weight, above all 0.12 to 1% by weight as Na. It is disadvantageous to reduce the sodium content to 0.07% by weight or less as described in Japanese Laid-Open Patent Publication No. 89843/1981.

The reaction of converting ethylene into ethylene oxide with the catalyst of this invention can be carried out by a conventional operating method. For example, the reaction pressure is 1 to 35 kg/$cm^2$, and the reaction temperature is 180° to 300° C., preferably 200° to 260° C. Ethylene is used in an amount of 1 to 30% by volume, and oxygen, 1 to 20% by volume. Generally, the presence of a predetermined amount, for example, up to 70% by volume, of a diluent such as methane is preferred. Oxygen may be fed in the form of air or industrial oxygen. By adding a reaction modifier such as ethylene dichloride, the formation of hot spots in the catalyst can be prevented and the performance of the catalyst, particularly its selectivity, can be greatly improved. The amount of the reaction modifier is preferably several to several tens of ppm.

The following Examples and Comparative Examples illustrate the present invention.

EXAMPLES 1-3 AND COMPARATIVE EXAMPLE 1

In each run, a catalyst was prepared by using an alpha-alumina carrier (a ring-like shape having a size of 80×30×8 mm; surface area 1 $m^2/g$, pore volume 0.4 ml/g; average pore diameter 1.9 micrometers) having each of the different $SiO_2$ and Na contents indicated in Table 1 by the following method.

Sodium carbonate (13.2 g) was dissolved in 1 liter of water, and 1 kg of the carrier was immersed in it. The excess of the solution was removed from the carrier by dripping. The carrier was then dried for 15 minutes with superheated steam at 140° C.

AgNO₃ (228 g) and 135 g of potassium oxalate (K₂C₂O₄.H₂O) were dissolved each in 1 liter of water and then mixed. The mixture was heated to 60° C. in a water bath to obtain a white precipitate of silver oxalate. After filtration, the precipitate was washed with distilled water to remove potassium from it. Separately, 200 ml of an aqueous solution was prepared by dissolving 19.8 g of 1,3-propanediamine and 72.2 g of ethylenediamine, and with ice cooling, added little by little to the silver oxalate precipitate to prepare a silver oxalate/amine complex solution. It was mixed with 40 ml of an aqueous solution containing 0.065 g of barium hydroxide and 0.720 g of cesium chloride. Water was added to adjust the entire volume to 378 ml. The solution was then transferred to a rotary evaporator. After impregnating Na₂CO₃, all the previously prepared dry carrier was added. Impregnation was carried out at 50° C. while rotating the evaporator. In the early stage of the impregnating operation, the pressure was reduced to 100 mmHg, and 5 minutes after the pressure was returned to atmospheric pressure, the impregnated carrier was taken out. The carrier was heated with superheated steam at 200° C. for 10 minutes at a flow rate of 2 m/second to prepare a catalyst of this invention. The amounts of Ag, Na, Ba, Cs and Cl deposited were 12%, 0.2%, 50 ppm, 473 ppm and 126 ppm, respectively.

The catalyst so prepared was pulverized to a size of 6 to 10 mesh, and 3 ml of it was charged in a steel reaction tube having an inside diameter of 7.5 mm. A reaction gas composed of 30% by volume of ethylene, 8% by volume of oxygen, 1.5 ppm of vinyl chloride and the balance being nitrogen was passed through the reaction tube under 18 kg/cm²-G at a SV of 4,000 h⁻¹. The reaction temperature $T_{40}$ (° C., bath temperature) at which the contemperature version of oxygen became 40% after the lapse of one week and the selectivity $S_{40}$ of ethylene oxide based on ethylene at the time when the conversion of oxygen reached 40% are shown in Table 1. It is seen from the table that the catalysts of the invention have higher activity and selectivity than the catalyst in the comparative example which had a lower SiO₂ content. It is also seen that the catalyst having an SiO₂ content of 12% (Example 3) has slightly inferior activity and selectivity compound to the catalysts having an SiO₂ content of 3 and 6% (Examples 1 and 2). X-ray diffraction analysis showed that only alphaalumina crystals exist in the carrier of Comparative Example 1, but the carriers of Examples 1 to 3 contained Al₆Si₂O₁₃ crystals in addition to alpha-alumina.

With Methyl Red having a pKa of +4.8, the carriers of Examples 1 to 3 showed an acidic color in toluene solvent, and by titration with n-butylamine, the amount of acid on the carriers of Examples 1 to 3 was about 1 micromole/g. The carrier of Comparative Example 1, however, did not show an acidic color with the same dye. Carriers obtained by pre-impregnating the carriers used in the Examples with Na₂CO₃ and subsequent drying did not at all show an acidic color, and this clearly shows that the acid sites of the carriers were masked by the deposition of sodium carbonate. It was found on the other hand that the deposition of sodium carbonate changed the color of Bromothymol Blue having a pKb of +7.1 and the carriers showed basicity (a carrier without Na deposited thereon had no basic site).

TABLE 1

| Example | SiO₂ content of the carrier (wt. %) | Silica content per surface area (wt. %/m²/g) | Na content of the carrier (wt. %) | $T_{40}$ (°C.) | $S_{40}$ (%) |
|---|---|---|---|---|---|
| 1 | 3 | 3 | 0.20 | 213 | 82.1 |
| 2 | 6 | 6 | 0.20 | 213 | 81.9 |
| 3 | 12 | 12 | 0.20 | 217 | 81.6 |
| CEx. 1 | 0.3 | 0.3 | 0.015 | 217.5 | 80.3 |

*CEx.: Comparative Example.

EXAMPLE 4

A catalyst was prepared by the following method using the carrier (SiO₂ content 3% by weight, Na content 0.20% by weight) used in Example 1.

AgNO₃ (217 g) and 129 g of potassium oxalate (K₂C₂O₄.H₂O) were each dissolved in 1 liter of water and then mixed. The mixture was heated to 60° C. in a water bath to obtain a well crystallized precipitate of silver oxalate. After filtration, the precipitate was washed with distilled water to remove potassium from it. Separately, 200 ml of an aqueous solution was prepared by dissolving 18.9 g of 1,3-propanediamine and 68.8 g of ethylenediamine, and with ice cooling, added little by little to the silver oxalate precipitate to prepare a silver oxalate/amine complex solution. It was mixed with 40 ml of an aqueous solution containing 0.686 g of cesium chloride. Water was added to adjust the volume of the mixture to 400 ml. The mixture was then transferred to a rotary evaporator, and 950 g of the carrier used in Example 1 (not containing sodium carbonate deposited thereon) was added and impregnated at 50° C. while rotating the evaporator. In the early stage of the impregnating operation, the pressure was returned to 100 mmHg. Five minutes after the pressure was returned to atmospheric pressure, the impregnated carrier was transferred to a wire cage to remove the excess of the solution. Furthermore, it was left to stand for 2 hours to remove the solution, and then heated with superheated steam at 200° C. for 10 minutes at a flow rate of 2 m/sec. The amounts of Ag, Cs and Cl deposited were 12%, 473 ppm and 126 ppm, respectively. These values agreed with the amounts of these components deposited which had been calculated from the concentrations of Ag, Cs, Cl in the impregnating solution left after the above impregnation and the porosity of the catalyst.

The catalyst was pulverized to a size of 6 to 10 mesh, and used in the same reaction as in Example 1. $T_{40}$ was 220° C., and S was 81.2%.

EXAMPLE 5

A catalyst was prepared in the same way as in Example 1 except that barium was not added. The amounts of Ag, Na, Cs and Cl deposited were 12%, 0.2%, 473 ppm and 126 ppm, respectively.

COMPARATIVE EXAMPLES 2-3

Catalysts were prepared in the same way as in Example 1 except that alpha-alumina carriers (a ring-like shape having a size of 80×30×8 mm; surface area 0.44 m²/g; pore volume 0.37 ml/g; average pore diameter 3.0 micrometers) having different SiO₂ contents and a surface area outside the scope of the invention were used, and the amounts of the cation components charged were changed (the amounts of the cation components charged were determined so as to give an optimum composition in these catalyst systems). The compositions of the catalysts are shown in Table 2.

Using the resulting catalysts, the same reaction as in Example 1 was carried out. The results are also shown in Table 2. It is seen that the catalysts obtained in these examples are inferior in activity and selectivity to the catalyst obtained in Example 1. Furthermore, in these catalyst systems, the effect of including $SiO_2$ is not clearly seen.

TABLE 2

| Comparative Example | Carrier | | | Catalyst composition | | | | | Results of the reaction | |
|---|---|---|---|---|---|---|---|---|---|---|
| | $SiO_2$ content (wt. %) | Silica content per specific surface area (wt. %/m$^2$/g) | Na content (wt. %) | Ag (wt. %) | Na (wt. %) | Cs (ppm) | Ba (ppm) | Cl (ppm) | $T_{40}$ (°C.) | $S_{40}$ (%) |
| 2 | 4.4 | 10 | 0.20 | 12 | 0.4 | 158 | 50 | 42 | 222 | 80.0 |
| 3 | 0.2 | 0.45 | 0.20 | 12 | 0.4 | 158 | 50 | 42 | 223 | 79.8 |

EXAMPLES 6–9

Catalysts were prepared in the same way as in Example 1 except that alpha-alumina carriers (a ring-like shape having a size of 80×30×8 mm; surface area 1 m$^2$/g; pore volume 0.36 ml/g; average pore diameter 2.1 micrometers) having different $SiO_2$ and Na contents indicated in Table 3 were used. The amounts of Ag, Na, Ba, Cs and Cl deposited were 12%, 0.2%, 50 ppm, 473 ppm and 126 ppm, respectively.

Each of the catalysts was pulverized to a size of 6 to 10 mesh, and filled in a steel reaction tube having an inside diameter of 3 ml. A reaction gas composed of 30% by volume of ethylene, 8.5% by volume of oxygen, 6% by volume of carbon dioxide, 1.5 ppm of vinyl chloride and the balance being nitrogen was passed through the reaction tube under a pressure of 14.5 kg/cm$^2$-G at a SV of 4,000 h$^{-1}$ $T_{40}$ and $S_{40}$ are shown in Table 3. It is seen that the performances of the catalysts were nearly equivalents when the $SiO_2$ content was 1 to 3% and the Na content was 0.12 to 1%, but that when the $SiO_2$ content was 0.6%, $S_{40}$ was slightly lower.

COMPARATIVE EXAMPLE 4

A catalyst was prepared in the same way as in Example 1 except that an alpha-alumina carrier having a $SiO_2$ content of 0.3% by weight and a Na content of 0.26% by weight (a ring-like shape having a size of 80×30×8 mm; surface area 1 m$^2$/g; pore volume 0.36 ml/g; average pore diameter 2.0 micrometers) was used. The amounts of Ag, Na, Ba, Cs and Cl deposited were 12%, 0.2%, 50 ppm, 473 ppm, and 126 ppm.

Using the catalyst, the same reaction as in Example 6 was carried out. The results are shown in Table 3. It is seen that the catalyst has higher activity, but much lower selectivity, than the catalyst of Example 8.

EXAMPLE 10 AND COMPARATIVE EXAMPLE 5

Catalysts were prepared in the same way as in Example 1 except that alpha-alumina carriers (a ring-like shape having a size of 80×30×8 mm; surface area 1.3 m$^2$/g; pore volume 0.4 ml/g; average pore diameter 1.5 micrometers; $SiO_2$ content 3% by weight) having different Na contents indicated in Table 4 were used. The amounts of Ag, Na, Ba, Cs and Cl deposited were 12%, 0.2%, 50 ppm, ppm, and 126 ppm, respectively.

Using these catalysts, the same reaction as in Example 6 was carried out. The results are shown in Table 4. It is seen that the catalyst of Comparative Example 5 having a low Na content had much lower activity, and lower selectivity, than the catalyst of Example 10. The carrier used in Comparative Example 5 showed a stronger acidic color in toluene with Dimethyl Yellow having a pKa of +3.3 than the carrier used in Example 10. Although it is not entirely clear what brought about the difference in performance between the two catalysts, we assume that it is partly attributed to the difference in acidity between the carriers used.

TABLE 3

| Example | Carrier | | $T_{40}$ (°C.) | $S_{40}$ (%) |
|---|---|---|---|---|
| | $SiO_2$ content (wt. %) | Na content (wt. %) | | |
| 6 | 0.6 | 0.26 | 225 | 79.5 |
| 7 | 1.5 | 0.12 | 224 | 80.5 |
| 8 | 3 | 0.26 | 225 | 80.6 |
| 9 | 5.5 | 1.0 | 225 | 80.2 |
| CEx. 4 | 0.3 | 0.26 | 220 | 77.7 |

TABLE 4

| Example | Carrier | | $T_{40}$ (°C.) | $S_{40}$ (%) |
|---|---|---|---|---|
| | $SiO_2$ content (wt. %) | Na content (wt. %) | | |
| 10 | 3 | 0.35 | 219 | 80.3 |
| CEx. 5 | 3 | 0.05 | 229 | 79.3 |

What is claimed is:

1. A silver-deposited catalyst for production of ethylene oxide by oxidizing ethylene, said catalyst comprising as catalyst ingredients silver and a cation component selected at least from sodium, potassium, rubidium and cesium, and a carrier composed mainly of alpha-alumina, said carrier having:
   (1) a surface area of 0.8 to 2m$^2$/g,
   (2) acidity that can be detected by an indicator having a pKa of +4.8,
   (3) a water absorption of 20 to 50%,
   (4) a silica content of 0.5 to 12% by weight,
   (5) a silica cointent, per m$^2$/g of surface area, of 0.5 to 12 % by weight,
   (6) a sodium content of 0.08 to 2% by weight, and
   (7) a crystal of $Al_6Si_2O_{13}$ which can be detected by X-ray diffraction analysis.

2. The catalyst of claim 1 wherein the cation component is composed of (A) sodium and (B) at least one of potassium, rubidium and cesium.

3. The catalyst of claim 1, wherein the cation component is composed of (A) sodium, (B) at least one of potsassium, rubidium and cesium and (C) barium.

4. The catalyst of claim 1 wherein the cation component has been deposited on the carrier from aqueous solution.

5. The catalyst of claim 1, wherein during production of said catalyst, silver and/or the cation component is impregnated in the carrier and heat-treated in superheated steam at 130° to 300° C.

6. The catalyst of any one of claims and 1 and 2 to 5 wherein the carrier has a surface area of 0.8 to 1.7 m²/g.

7. The catalyst of any one of claims 1 and 2 to 5 wherein the carrier has an average pore diameter of 0.9 to 3.5 micrometers.

8. The catalyst of any one of claims 1 and 2 to 5 wherein the carrier has a silica content of 1 to 12% by weight.

9. The catalyst of claim 6 wherein the carrier has an average pore diameter of 0.9 to 3.5 micrometers.

10. The catalyst of claim 6 wherein the carrier has a silica content of 1 to 13% by weight.

11. The catalyst of claim 7 wherein the carrier has a silica content of 1 to 12% by weight.

12. The catalyst of claim 1 wherein the carrier has a silica content, per m²/g of surface area, of 1 to 8% by weight.

* * * * *